(12) United States Patent
Perez et al.

(10) Patent No.: US 6,589,953 B2
(45) Date of Patent: *Jul. 8, 2003

(54) INDOLE DERIVATIVES AS 5-HT1B AND 5-HT1D AGONISTS

(75) Inventors: Michel Perez, Castres (FR); Serge Halazy, Lagarrigue (FR)

(73) Assignee: Pierre Fabre Medicament, Boulogne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/903,469

(22) Filed: Jul. 11, 2001

(65) Prior Publication Data

US 2002/0061891 A1 May 23, 2002

Related U.S. Application Data

(63) Continuation of application No. 09/486,258, filed on Feb. 23, 2000, now Pat. No. 6,277,853.

(30) Foreign Application Priority Data

Aug. 25, 1997 (FR) .............................. 97 10606

(51) Int. Cl.$^7$ .................. C07D 403/12; C07D 401/02; C07D 417/14; A61K 31/495
(52) U.S. Cl. .................. 514/252.19; 544/295; 544/366; 544/364; 544/367; 544/369; 544/368; 544/254.05; 544/253.01; 544/254.03; 544/254.02; 514/254.05; 514/253.01; 514/254.03; 514/254.02
(58) Field of Search .................. 544/367, 369, 544/295, 366, 364, 368; 514/254.03, 254.02, 252.19, 254.05, 253.01

(56) References Cited

FOREIGN PATENT DOCUMENTS

| FR | 2 699 918 A | 7/1994 |
|----|-------------|--------|
| WO | 95 14004 A  | 5/1995 |

OTHER PUBLICATIONS

Robichaud et al. Recent Advances in Selective Serotonin Receptor Modulation, Med. Chem., 35: 11–20, Jan. 2000.*
C.M. Perry, et al., Drugs 55(6), pp 889–922 (Jun. 1998).
S. Ahleinus, et al., Psychopharmacology (Berl), 137(4), pp 374–382, (Jun. 1998).
S. Ahlenius, et al., Eur J Pharmacol 379(1), pp 1–6, (Aug. 20, 1999).
Paredes RG, et al., J Neural Transm, 107(7), pp 767–777, (2000).
Y.Y. Huang, et al., Neuropsychopharmacology, 21(2), pp 238–246, (1999).
A. Meneses, Rev Neurosci, 9(4), pp 275–289, (1998).
C.M. Perry, et al., Drugs 55(6), pp 889–922 (Jun. 1998).
S. Ahleinus, et al., Psychopharmacology (Berl), 137(4), pp 374–382, (Jun. 1998).
S. Ahlenius, et al., Eur J Pharmacol 379(1), pp 1–6, (Aug. 20, 1999).
Paredes RG, et al., J Neural Transm, 107(7), pp 767–777, (2000).
Y.Y. Huang, et al., Neuropsychopharmacology, 21(2), pp 238–246, (1999).
A. Meneses, Rev Neurosci, 9(4), pp 275–289, (1998).

* cited by examiner

Primary Examiner—Richard L. Raymond
Assistant Examiner—Hong Liu
(74) Attorney, Agent, or Firm—The Firm of Hueschen and Sage

(57) ABSTRACT

The invention concerns novel indole piperazine derivatives of formula (I). It also concerns a method for preparing said compounds and their use as therapeutically active substances, in particular for treating or preventing diseases related to the disfunction of 5-HT$_{1-like}$ receptors.

13 Claims, No Drawings

INDOLE DERIVATIVES AS 5-HT1B AND 5-HT1D AGONISTS

This application is continuation of U.S. application Ser. No. 09/486,258, filed Feb. 23, 2000. now U.S. Pat. No. 6,277,853

The present invention relates to novel heterocyclic compounds derived from indole piperazines as well as their method of preparation, the pharmaceutical compositions containing them and their use as medicament.

Serotonin or 5-hydroxytryptamine (5-HT) plays an important role both at the level of the nervous system and at the cardiovascular level. Serotoninergic receptors have been identified both at the central and peripheral level. It is generally accepted that serotonin plays an important role in various types of pathological conditions such as

- certain psychiatric disorders such as anxiety, depression, aggressiveness, panic attacks, obsessive-compulsive disorders, schizophrenia, suicidal tendency,
- certain neurodegenerative disorders such as Alzheimer's disease, Parkinsonism,
- migraine, cephalagia, and
- disorders linked to alcoholism (cf. E. Zifa, G. Fillion, Pharm. Reviews, 44, 401, 1992; A. Moulignier, Rev. Neuro. (Paris) 150, 3–15, 1994; S. Langer, N. Brunello, G. Racagni, J. Mendlecvicz, "Serotonin receptor subtypes: pharmacological significance and clinical implications" Karger Ed.; (1992); B. E. Leonard, Int. Clin. Psychopharmacology, 7, 13–21 (1992); R. W. Fuller; J. Clin. Psychiatry, 53, 36–45 (1992); D. G. Grahame-Smith, Int. Clin, Psychopharmacology, 6. suppl. 4, 6–13, (1992).

The compounds according to the present invention are novel compounds having a very high affinity and a very good selectivity for the receptors commonly called $5\text{-HT}_{1\text{-like}}$ and more particularly for the receptors called $5\text{-HT}_{1B}$ and $5\text{-HT}_{1D}$.

The medicaments, alone or in combination with other therapeutic agents, including one or more active ingredients of the present invention find their use in the treatment, both curative and preventive, of diseases related to the dysfunction of the $5\text{-HT}_{1\text{-like}}$ receptors including the $5\text{-HT}_{1B}$ and $5\text{-HT}_{1D}$ receptors, to their deregulation, or to modifications of the activity of the endogenous ligand which is generally serotonin.

The compounds of the present invention are potent agonists, both at the level of their affinity and at the level of their intrinsic efficacy or activity, and selective agonists for the $5\text{-HT}_{1B}$ and $5\text{-HT}_{1D}$ receptors. The agonists for the $5\text{-HT}_{1\text{-like}}$ receptors, and more particularly for the $5\text{-HT}_{1B}$ receptors, exhibit a selective vasoconstrictive activity and find their use in the treatment of migraine and of vasospastic disorders (A. Doenicke et al., The Lancet, 1, 1309–1311, 1988; M. D. Ferrari, P. R. Saxena, Cephalalgia, 13, 151–165, 1993; S. J. Peroutka, Headache, 30, 5–11, 1990; M. A. Moskowitz, TiPS, 13, 307–311, 1992; W. Feniuk, P. P. Humphrey, M. S. Perren, H. E. Connor, E. T. Whalley, J. Neurol. 238, pp. 57–61, 1991; A. V. Deligonis, S. J. Peroutka, Headache, 31, 228–231, 1991).

The compounds of the present invention, which are for the most part potent and selective agonists for the $5\text{-HT}_{1B}$ and $5\text{-HT}_{1D}$ receptors, therefore find their use more particularly in the curative and prophylactic treatment of attacks of conventional migraine, with aura, of common migraine, without aura, vascular facial pain, chronic vascular cephalalgia and vasospastic disorders.

The prior state of the art in this field is illustrated in particular by:

- patent applications EP-A2-0303507, WO 93/14087, WO 94/02460, WO 92/14708, and patents U.S. Pat. No. 4,839,377, GB-A-2124210 and GB-A-2162532 which describe sulfonamides derived from typtamines, including sumatriptan, as antimigraine drugs,
- patent applications GB-A-2191488, GB-A-2185020 and GB-A-2168347 which describe alkylamides derived from tryptamine.
- French patent applications FR-A-2,699,918 and FR-A-2,707,639 which describe novel indole compounds derived respectively from piperazines and arylamines as ligands for the $5\text{-HT}_{1B}$ and $5\text{-HT}_{1D}$ receptors.
- Application for patent of invention FR-A-2,724,933 which describes novel aromatic ethers derived from indole as ligands for the $5\text{-HT}_{1D}$ receptors.
- European patent applications EP-A-0313397, EP-A-0486666, EP-A1-0494774, EP-A-0494774, EP-A2-0497512, EP-A1-0501568, EP-A-0464558, EP-A1-0548813 and international applications WO 92/13856 and 93/11106 which describe heterocyclic derivatives derived from tryptamine as agonists for the $5\text{-HT}_{1\text{-like}}$ receptors.

The present invention describes a novel class of piperazines derived from aminoindole which is distinguishable from all the closest prior art derivatives by their novel and different chemical structure, but also by their biological profile and their therapeutic potential since many compounds according to the present invention exhibit a very high affinity and selectivity for the $5\text{-HT}_{1B}$ and $5\text{-HT}_{1D}$ receptors, a remarkable efficacy and a particularly advantageous hemodynamic profile. The derivatives of the present invention therefore find their usefulness more particularly as active ingredients of medicinal compositions for the treatment of migraine and of various similar disorders.

The present invention relates to compounds of general formula (I).

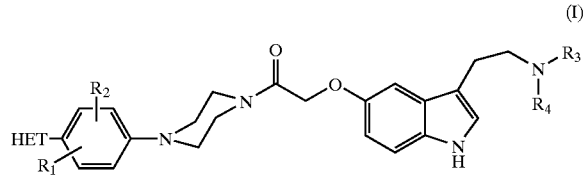

in which,

HET represents a heterocycle chosen from

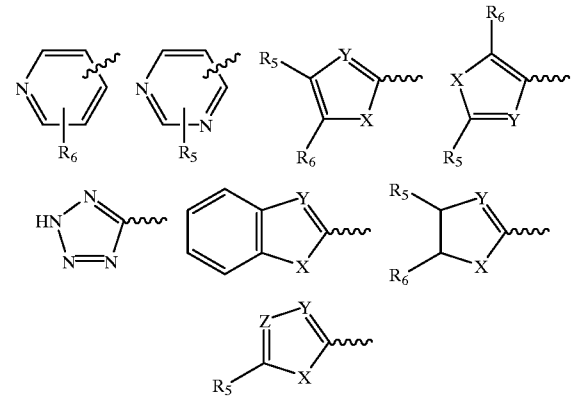

$R_1$ and $R_2$, which are identical or different, represent a hydrogen atom, $R'_1$, $CF_3$, $CH_2CF_3$, $C_6H_5$, $CH_2C_6H_5$, OH, OR′$_1$, SH, SR′$_1$, Cl, F, Br, I, CN, NH$_2$, NHR′$_1$, NR′$_1$R′$_2$, NO$_2$, NH—NH$_2$, NH—NHR′$_1$, NHOH, NHCO$_2$R′$_1$, NHCONH$_2$, NHCONR′$_1$R′$_2$, NHSO$_2$R′$_1$, SO$_2$R′$_1$, SO$_2$NH$_2$, SO$_2$NHR′$_1$, COR′$_1$, CO$_2$R′$_1$, CONH$_2$, CONHR′$_1$, CONR′$_1$R′$_2$ which may be at the ortho or meta position on the aromatic ring, R$_3$ and R$_4$, which are identical or different, represent a hydrogen atom, a linear or branched carbon-containing radical comprising from 1 to 6 carbon atoms or a benzyl or phenethyl residue, Y and Z, which are identical or different, represent CH or N, X represents O, S or NR$_7$, R$_5$, R$_6$ and R$_7$, which are identical or different, represent a hydrogen atom, a linear or branched alkyl residue comprising from 1 to 6 carbon-atoms or a phenyl residue which is optionally substituted with a linear or branched alkyl residue comprising from 1 to 6 carbon atoms, a halogen atom, CF$_3$, OCH$_3$, CN or NO$_2$, R′$_1$ and R′$_2$, which are identical or different, represent a linear or branched alkyl group comprising from 1 to 6 carbon atoms or a phenyl residue which is optionally substituted with a linear or branched alkyl residue comprising from 1 to 6 carbon atoms, Cl, Br, F, I, OCH$_3$, OH, NO$_2$, SCH$_3$, as well as their salts, solvates and bioprecursors which are acceptable for therapeutic use.

The expression "bioprecursors" as used in the present invention applies to compounds whose structure differs from that of the compounds of formula (I) but which, when administered to an animal or to a human being, are converted in the body to a compound of formula (I).

Among the compounds of general formula (I) which are included in the present invention, a class of compounds which is particularly appreciated corresponds to the compounds of general formula (I) in which R$_1$, R$_2$, R$_3$ and R$_4$ each represent a hydrogen atom.

Another class of compounds included in the present invention which is particularly appreciated corresponds to the compounds of general formula (I) in which HET represents a pyridyl or pyrimidyl residue.

A third class of compounds included in the present invention which is particularly appreciated corresponds to the compounds of general formula (I) in which HET represents a 5-membered heterocycle containing from 1 to 3 heteroatoms chosen from O, S or N.

Among the compounds of general formula (I) in the form of salts which are acceptable for therapeutic use, the salts formed by addition with inorganic acids, chosen from the hydrochlorides, hydrobromides, sulfates, fumarates, maleates, methanesulfonates and succinates, are preferred.

Other salts may be used in the preparation of the compounds of formula (I), for example the adducts with creatinine sulfate.

The present invention also relates to a method of preparing the compounds of general formula (I) which consists in the condensation of an aromatic piperazine of general formula (II)

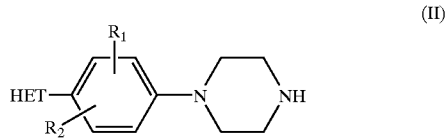

(II)

in which HET, R$_1$ and R$_2$ are defined as in general formula (I) with a carboxylic acid or a carboxylic acid derivative of general formula (III)

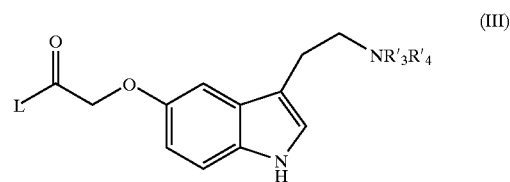

(III)

in which R′$_3$ and R′$_4$ are identical respectively to R$_3$ and R$_4$ which are defined as in general formula (I), or R′$_3$ or R′$_4$ are precursors of or protecting groups for R$_3$ and R$_4$ which will be converted to R$_3$ and R$_4$ following the condensation of (II) with (III), and L represents OH, Cl, O-alkyl or the group —C(=O)L which represents the activated form of a carboxylic acid appropriate for the formation of an amide by reacting with an amine.

A particularly appreciated variant of the method of preparation of the invention uses an amine of formula (II) and a compound of formula (III) in which L represents Cl, in the presence of an organic or inorganic base such as pyridine, DMAP, DBU, K$_2$CO$_3$, Cs$_2$CO$_3$ or Na$_2$CO$_3$ in a polar aprotic anhydrous solvent such as THF, DME, dichloromethane, at a temperature of between −20° C. and 40° C.

A second particularly appreciated variant of the method of preparation of the invention uses the condensation of an amine of formula (II) with a compound of formula (III) in which L represents OH, in the presence of a tertiary amine such as triethylamine, diisopropylethylamine, pyridine, DMAP, N-methyl-morpholine, in a polar aprotic solvent such as THF, dichloromethane, DCE, ethyl acetate, chloroform, DMF, by reacting with an activating agent such as EDC, DCC, BOP, PyBOP, at a temperature of between −10 and 35° C.

A method which is particularly appreciated in the context of this second variant consists in treating the compound of formula (III) in which L represents OH with ethyl chloroformate in the presence of a base such as, for example, a tertiary amine such as N-methylmorpholine, in a polar aprotic solvent such as dichloromethane, dichloroethane, THF and DME, at a temperature of between −20° C. and 0° C. followed by the addition of the amine of general formula (II).

In the specific case of the compounds of formula (I) in which R$_3$ and R$_4$ represent a hydrogen atom, the method of synthesis consists in condensing a heteroaromatic piperazine of general formula (II) with a carboxylic acid or a derivative of this carboxylic acid of general formula (III) in which R′$_3$ represents a hydrogen atom and R′$_4$ represents a protecting group t-butoxycarbonyl according to the methods and techniques previously described and then hydrolyzing the protecting group t-butoxycarbonyl in acidic medium, with the aid, for example, of hydrochloric acid or trifluoroacetic acid.

Another method of preparing the compounds of general formula (I) included in the present invention consists in converting an arylpiperazide derived from tryptamine of general formula (IV)

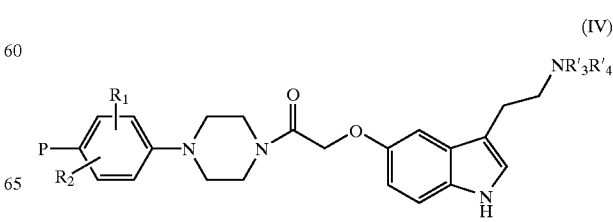

(IV)

in which $R_1$ and $R_2$, $R'_3$ and $R'_4$ are defined as above and P represents $OSO_2CF_3$, Br, I or CN to a compound of general formula (I) by various methods and techniques which will depend essentially on the nature of P in the precursor (IV) and on the nature of HET in the compound of general formula (I).

Accordingly, the compounds of general formula (IV) in which P represents I, Br or $OSO_2CF_3$ may be converted to compounds of general formula (I) by condensation with a boronic acid of formula HEP-B(OH) 2 in the presence of palladium according to the method well known to persons skilled in the art termed "Suzuki coupling".

The compounds of general formula (IV) in which P represents CN are used as precursors of various compounds of general formula (I) as explained in the following scheme:

The aromatic piperazines of general formula (II) are prepared by various methods and techniques well known to persons skilled in the art for preparing arylpiperazines. In general, these intermediate piperazines are prepared from a precursor of general formula (V)

(V)

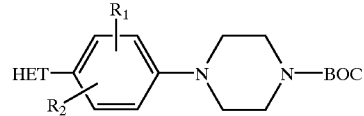

in which HET, $R_1$ and $R_2$ are as described above, by reaction with an acid such as hydrochloric acid or preferably trifluoroacetic acid.

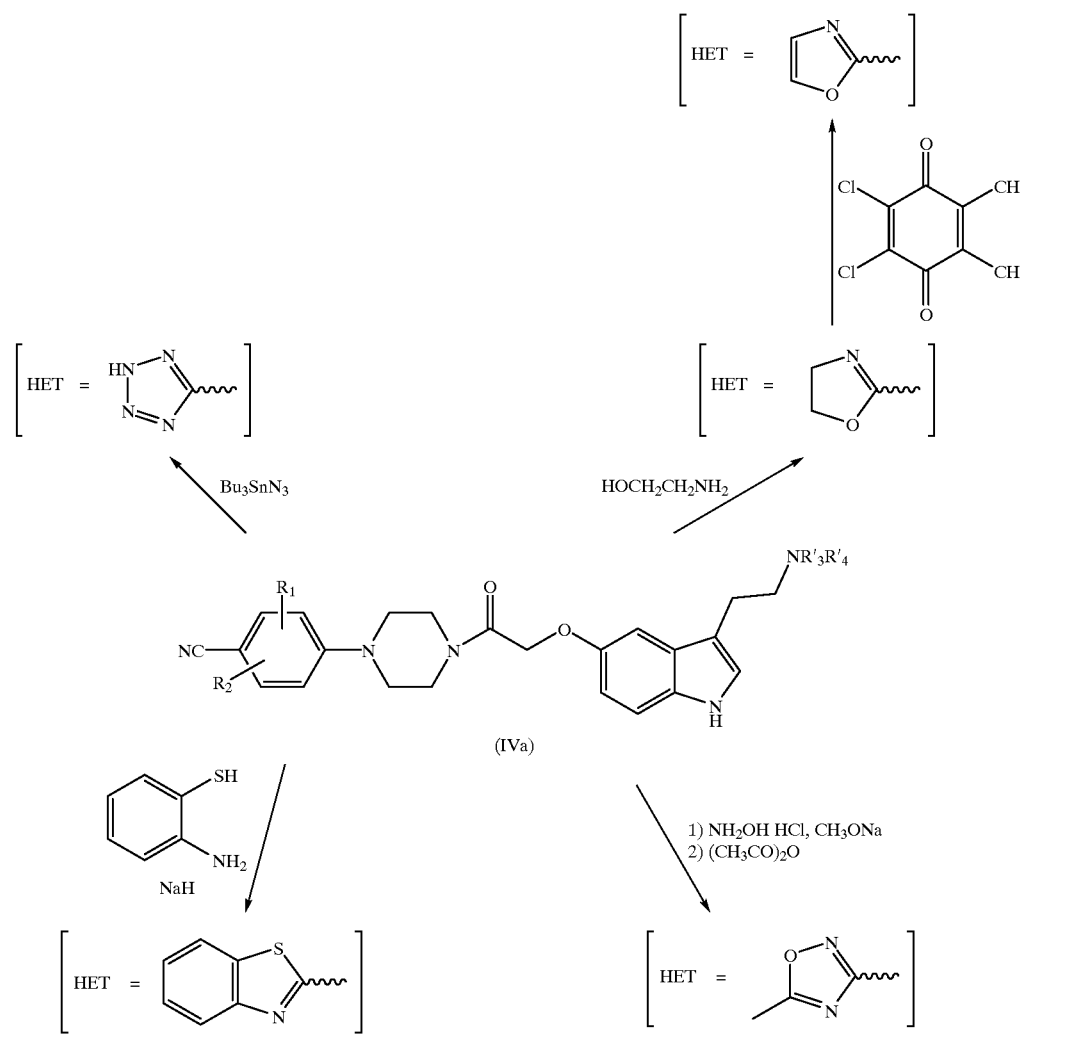

It is clearly understood that, in the case where $R'_3$ and $R'_4$ are different from $R_3$ and $R_4$, the conversions indicated in this scheme imply the use of additional reactions to convert $R'_3$, $R'_4$ to $R_3$, $R_4$. Accordingly, the preparation of the compounds of general formula (I) in which $R_3$ and $R_4$ represent a hydrogen atom by the methods described in the above scheme use a precursor of general formula (IV) in which $R'_3$=H and $R'_4$=COO$^t$Bu and an additional reaction intended to restore the primary amine such as the use of an acid such as hydrochloric acid or trifluoroacetic acid.

The intermediates of formula (V) are accessible from intermediates of general formula (VI)

(VI)

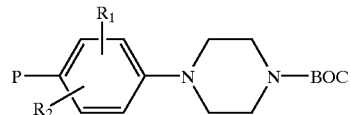

in which P is as described above.

The conversion of the arylpiperazines of formula (VI) to arylpiperazines of formula (V) is carried out by various methods and techniques described above for the conversion of the intermediates of general formula (IV) to compounds of formula (I).

In the specific case where, in general formula (V) at least one of the substituents $R_1$ or $R_2$ is an electron-attracting group, for example $NO_2$, $CF_3$, CN or $CO_2R$, attached at the ortho position on the aromatic ring with respect to the piperazine residue, an alternative method for obtaining the arylpiperazines of formula (V) consists in condensing N-BOC-piperazine with an electophile of general formula (VII).

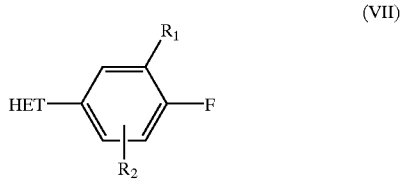

(VII)

in which HET and $R_2$ are as defined above and $R_1$ is an electron-attracting substituent, in the presence of an organic or inorganic base, at a temperature of between 20 and 100° C.

The intermediates of general formula (II) may also be prepared from anilines of general formula (VIII)

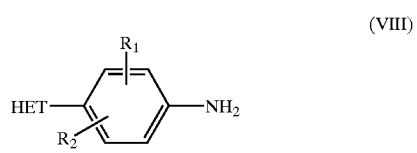

(VIII)

in which HET, $R_1$ and $R_2$ are defined as in general formula I, after reaction with electrophiles of formula (IX) or (X)

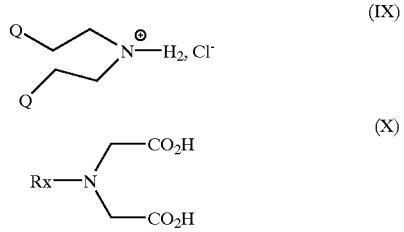

(IX)

(X)

in which Q represents a chlorine, a bromine, an iodine, a tosylate or a mesylate and $R_x$ represents an amine-protecting group, for example a t-butoxycarbonyl, which will be subsequently deprotected. The condensation of anilines of general formula (VIII) with electrophiles of general formula (IX) is preferably carried out in a polar anhydrous solvent such as DMF, acetonitrile, THF, butanol, t-butanol or DMSO, generally at the reflux temperature of the solvent used, in the presence of an organic or inorganic base such as potassium, sodium or calcium carbonate.

The intermediates of general formula (II) may also be prepared by condensation of anilines of general formula (VIII) with derivatives of aminodiacids of formula (X), in the presence of acetic anhydride, followed by the reduction of the intermediate diketopiperazide thus formed with, for example, a borane and finally cleavage of the protecting group, for example in acidic medium if a t-butoxycarbonyl residue is involved.

The methods which make it possible to convert a derivative of formula (I) to another derivative of formula (I) in which at least one of the substituents HET, $R_1$, $R_2$, $R_3$ or $R_4$ is different, by techniques and methods well known to persons skilled in the art should also be considered as being included in the present invention.

Accordingly and by way of example, the derivatives of general formula (I) in which $R_1$ represents an $NO_2$ group may be converted to derivatives of formula (I) in which $R_1$ represents $NH_2$ by methods and techniques well known for this type of reduction as described for example in Comprehensive Organic Transformation, R. C. Larock, V. C. H., p. 412 1989, among which there may be mentioned atmospheric hydrogenation catalyzed by palladium-on-carbon, the use of $SnCl_2$ or of zinc or alternatively rhodium catalyst in the presence of hydrazine. The compounds of formula (I) in which $R_1$ represents $NH_2$ may also be converted to derivatives of formula (I) in which $R_1$ represents $NR_8R_9$, $NHCO_2R_8$, $NHCOR_8R_9$, $NHSO_2R_8$, by methods and techniques well known to persons skilled in the art for converting an aromatic amine to amide, carbamate, urea or sulfonamide.

In the context of this invention, it is also necessary to consider the preparation of compounds of formula (I) from other compounds of formula (I) which are distinguishable by the nature of the HET-residue. Accordingly, the derivatives of general formula (I) in which HET represents a tetrazole residue may be converted to derivatives of formula (I) in which HET represents an oxadiazole according to-the scheme below:

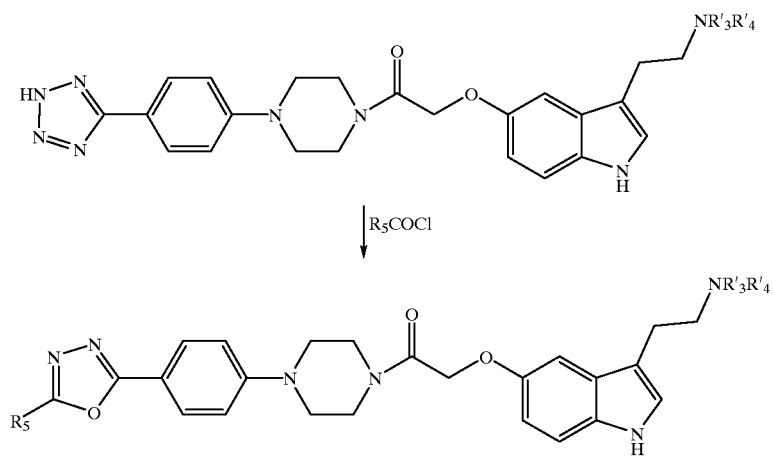

It is evident that in some chemical reactions or reaction sequences which lead to the preparation of compounds of general formula (I), it is necessary or desirable to protect possible sensitive groups in the side reactions. This may be achieved by the use, i.e. the introduction and the deprotection, of conventional protecting groups such as those described in "Protective Groups in Organic Synthesis", T. W. Greene, John Wiley & Sons, 1981, and "Protecting Groups", P. J. Kocienski. Thieme Verlag, 1994. The appropriate protecting groups will therefore be introduced and removed during the step most appropriate for doing this, using the methods and techniques described in the references cited above.

When it is desired to isolate a compound according to the invention in the form of a salt, for example an addition salt with an acid, this can be achieved by treating the free base of general formula (I) with an appropriate acid, preferably in an equivalent quantity.

The present invention also relates to the compounds of formula (I) for their application as therapeutically active substances.

The present invention relates more particularly to the compounds of formula (I) for the treatment or prevention of serotonin-related disorders, for the treatment or prevention of migraine, vascular facial pain, chronic vascular cephalalgia, for the treatment or prevention of depression, obsessive-compulsive disorders, bulimia, aggressiveness, alcoholism, nausea, sexual dysfunction, antisocial behavior, anxiety, spasticity, Alzheimer's and Parkinson's diseases.

The present invention also relates to the pharmaceutical compositions containing, as active ingredient, at least one compound of formula (I) and a pharmaceutically acceptable excipient.

The compositions according to the invention may be used by the oral, nasal, parenteral, rectal or topical route.

As solid compositions for oral administration, there may be used tablets, pills, powders in the form of gelatin capsules or cachets, granules. In these compositions, the active ingredient according to the invention is mixed with one or more inert diluents such as starch, cellulose, sucrose, lactose or silica, under an argon stream. These compositions may also comprise substances other than the diluents, for example one or more lubricants such as magnesium stearate or talc, a coloring, a coating or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than the diluents, for example wetting, sweetening, thickening, flavoring or stabilizing products.

The sterile compositions for parenteral administration may be preferably solutions which are aqueous or non-aqueous, suspensions or emulsions. As solvent or vehicle, it is possible to use water, propylene glycol, a polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. The sterilization may be performed in several ways, for example by aseticizing filtration, by incorporating sterilizing agents into the composition, by irradiation or by heating. They may also be prepared in the form of sterile solid compositions which may be dissolved at the time of use in sterile water or any other injectable sterile medium.

The compositions for rectal administration are suppositories or rectal capsules which contain, in addition to the active product, excipients such as cocoa butter, semi-synthetic glycerides or polyethylene glycols.

The compositions for topical administration may be, for example, creams, lotions, collyria, collutoria, nasal drops or aerosols.

The doses depend on the desired effect, the duration of the treatment and the route of administration used; they are generally between 0.001 g and 1 g, preferably between 0.005 g and 0.25 g per day, preferably by the oral route for an adult with unit doses ranging from 0.1 mg to 500 mg of active substance, preferably from 1 mg to 50 mg.

In general, the doctor will determine the appropriate dosage according to the age, weight and all the other factors specific to the subject to be treated.

The following examples illustrate the invention without, however, limiting the scope thereof.

EXAMPLE 1

2-[3-(2-Aminoethyl)-1H-indol-5-yloxy]-1-{4-[4-(5-phenyl-[1,3,4]oxadiazol-2-yl)phenyl]piperazin-1-yl}ethanone Fumarate

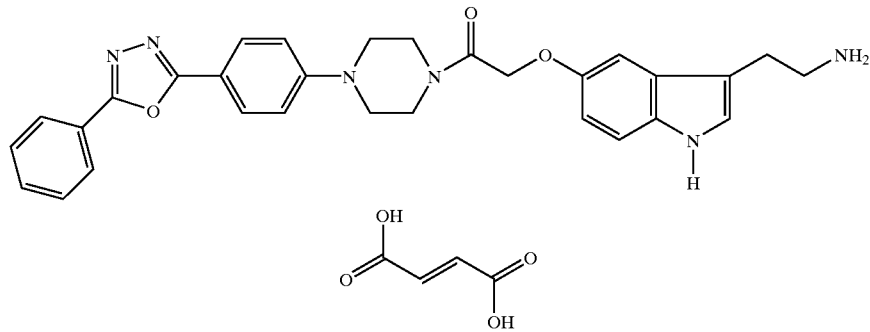

1A) N-tert-Butoxycarbonyl-4-(4-cyanophenyl)piperazine 1-(4-Cyanophenyl)piperazine (5.0 g; 26.7 mmol) in solution in dichloromethane (100 ml) in the presence of triethylamine (5.6 ml; 40.0 mmol) is treated with di-tert-butyl dicarbonate (6.4 g; 29.3 mmol). After stirring for 1 h at room temperature, the medium is diluted with dichloromethane and washed with water. The organic phase is dried over sodium sulfate, filtered and evaporated to dryness to give the intermediate 1A (7.7 g; 100%) in the form of a beige solid.

1B) N-tert-Butoxycarbonyl-4-[4-(2H-tetrazol-5-yl)phenyl]piperazine

The intermediate 1A (6.0 g; 20.8 mmol) in solution in xylene (76 ml), under nitrogen, is treated with trimethyltin azide (6.25 g; 31.3 mmol). After stirring for 24 h at 110° C., the reaction medium is brought to room temperature and the precipitate formed is filtered on sintered glass and then washed with toluene and with petroleum ether. This solid is purified by chromatography on a silica gel column eluted with a dichloromethane/methanol/ammonium hydroxide mixture in the proportions 80/19/1 to give compound 1B (5.75 g; 87%) in the form of a white solid.

1C) 1-[4-(5-Phenyl-[1,3,4]oxadiazol-2-yl)phenyl]piperazine

Compound 1B (1.5 g; 4.54 mmol) in solution in pyridine (15 ml) is heated at 60° C., under nitrogen, for 10 min. Benzoyl chloride (1.3 ml; 11.35 mmol) is then added and the mixture is heated under reflux for 3 h. To complete the reaction (0.5 ml; 4.54 mmol) of benzoyl chloride is again added and the mixture is heated for a further 1 h under reflux.

The reaction medium is then brought to room temperature, diluted with ethyl acetate, washed successively with water, with a saturated copper sulfate solution, with water and finally with a saturated sodium chloride solution. The organic phase is dried over sodium sulfate, filtered and evaporated to dryness.

The beige solid obtained is taken up in toluene (46 ml) and treated with trifluoroacetic acid (6 ml). After stirring for 1 h at room temperature, the medium is diluted with ethyl acetate, washed with sodium hydroxide (2N) and then with water and finally with a saturated sodium chloride solution. The organic phase is dried on sodium sulfate, filtered and evaporated to dryness. The syrup obtained is chromatographed on a silica gel column eluted with a dichloromethane/methanol/ammonium hydroxide mixture in the proportions 95/4.5/0.5 to give the pure compound 1C (800 mg; 57%).

proportions ranging from 8/1 to 4/1 to give the product of coupling (1.19 g; 84%). This compound is taken up in toluene (30 ml) and treated with trifluoroacetic acid (3.9 ml) at room temperature, for 1 h. The medium is diluted with ethyl acetate and then basified by addition of 2N sodium hydroxide.

The precipitate formed is isolated by filtration and then washed with water, with ethyl acetate and with ether. This solid is purified by chromatography on a silica gel column eluted with a dichloromethane/methanol/ammonium hydroxide mixture in the proportions 90/9/1 to give the expected product in the form of a base (746 mg; 75%).

This product is taken up in methanol and then salified by addition of fumaric acid (165 mg; 1.43 mmol) to give a white solid.

$^1$H NMR DMSO-d6 (ppm): 2.92 t, 2H; 3.03 t, 2H; 3.33–3.50 m, 4H; 3.60–3.75 m, 4H; 4.83 s, 2H; 6.41 s, 2H; 6.80 dd, 1H; 7.10–7.20 m, 4H; 7.26 d, 1H; 7.59–7.65 m, 3H; 7.96 d, 2H; 8.08–8.12 m, 2H; 10.81 s, 1H

| Elemental analysis ($C_{34}H_{34}N_6O_7 \cdot 1.5H_2O$) | | | |
|---|---|---|---|
| % calculated: | C 61.35 | H 5.60 | N 12.62 |
| % found: | C 61.14 | H 5.43 | N 12.70 |

Melting point: 170° C.

Mass spectrum: m/z 523 (MH$^+$)

EXAMPLE 2

2-[3-(2-Aminoethyl)-1H-indol-5-yloxy]-1-{4-[4-(5-o-tolyl-[1,3,4]oxadiazol-2-yl)phenyl]piperazin-1-yl}ethanone Fumarate

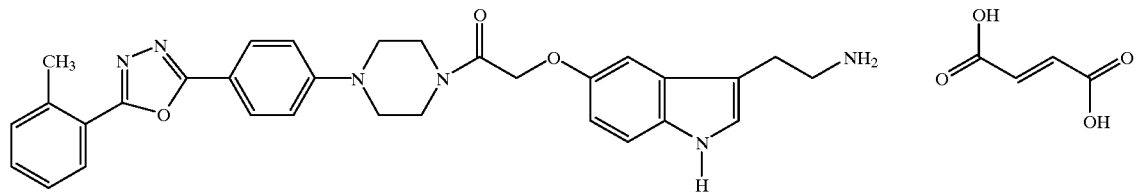
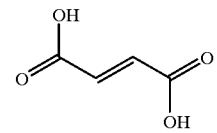

1) 2-[3-(2-Aminoethyl)-1H-indol-5-yloxy]-1-{4-[4-(5-phenyl-[1,3,4]oxadiazol-2-yl)phenyl]piperazin-1-yl}ethanone Fumarate 3-[2-(N-tert-Butoxycarbonyl)aminoethyl]-1H-indol-5-yloxyacetic acid (763 mg; 2.28 mmol), or SerBOC acid (Bioorg. Med. Chem. Lett., 5, 1995, 663–666), in solution in dichloromethane (9 ml), in the presence of N-methylmorpholine (0.27 ml; 2.50 mmol), is treated at −10° C. under nitrogen with ethyl chloroformate (0.24 ml; 2.50 mmol). After stirring for 10 min at −10° C., the intermediate 1C (769 mg; 2.50 mmol) is added and the mixture is stirred from −10° C. to room temperature for 2 h. The medium is diluted with ethyl acetate, washed successively with water, with a sodium bicarbonate solution and finally with a saturated sodium chloride solution. The organic phase is dried over sodium sulfate, filtered and evaporated to dryness.

The syrup obtained is chromatographed on a silica gel column eluted with a dichloromethane/acetone mixture in Compound 2 is prepared from intermediate 1B (1.0 g; 3.03 mmol), o-toluoyl chloride (0.99 ml; 7.55 mmol) and SerBOC acid (576 mg; 1.72 mmol) according to the procedure described for the preparation of Example 1.

$^1$H NMR DMSO-d6 (ppm): 2.68 s, 3H; 2.93 t, 2H; 3.04 t, 2H; 3.30–3.50 m, 4H; 3.60–3.75 m, 4H; 4.83 s, 2H; 6.42 s, 2H; 6.80 d, 1H; 7.11–7.20 m, 4H; 7.26 d, 1H; 7.40–7.53 m, 3H; 7.95 d, 2H; 8.04 d, 1H; 10.83 s, 1H

| Elemental analysis $C_{35}H_{36}N_6O_7 \cdot 1.5H_2O$ | | | |
|---|---|---|---|
| % calculated: | C 61.85 | H 5.78 | N 12.36 |
| % found: | C 62.07 | H 5.74 | N 12.26 |

Melting point: 123° C.

Mass spectrum: m/z 537 (MH$^+$)

EXAMPLE 3

2-[3-(2-Aminoethyl)-1H-indol-5-yloxy]-1-{4-[4-(5-p-tolyl-[1,3,4]oxadiazol-2-yl)phenyl]piperazin-1-yl}ethanone Fumarate

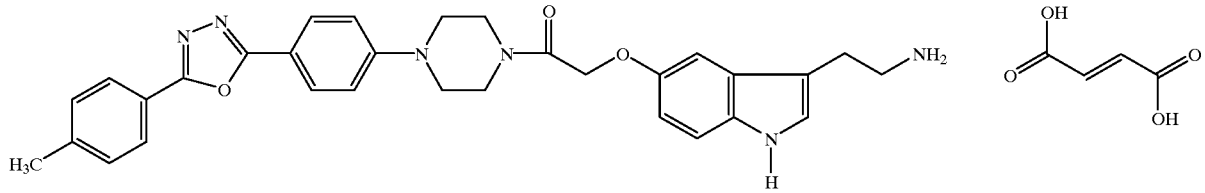

Compound 3 is prepared from intermediate 1B (900 mg; 2.72 mmol), p-toluoyl chloride (1.0 ml; 7.6 mmol) and SerBOC acid (186 mg; 0.55 mmol) according to the procedure described for the preparation of Example 1.

$^1$H NMR DMSO-d6 (ppm): 2.41 s, 3H; 2.94 t, 2H; 3.03 t, 2H; 3.32–3.48 m, 4H; 3.65–3.71 m, 4H; 4.84 s, 2H; 6.42 s, 2H; 6.80 dd, 1H; 7.10–7.18 m, 3H; 7.20 s, 1H; 7.27 d, 1H; 7.43 d, 2H; 7.98 dd, 4H; 10.83 s, 1H

| Elemental analysis $C_{35}H_{36}N_6O_7.2H_2O$ | | | |
|---|---|---|---|
| % calculated: | C 61.04 | H 5.85 | N 12.20 |
| % found: | C 60.84 | H 5.60 | N 12.07 |

Mass spectrum: m/z 537 (MH$^+$)
Melting point: 135° C.

EXAMPLE 4

2-[3-(2-Aminoethyl)-1H-indol-5-yloxy]-1-{4-[4-(5-methyl-[1,3,4]oxadiazol-2-yl)phenyl]piperazin-1-yl}ethanone Fumarate

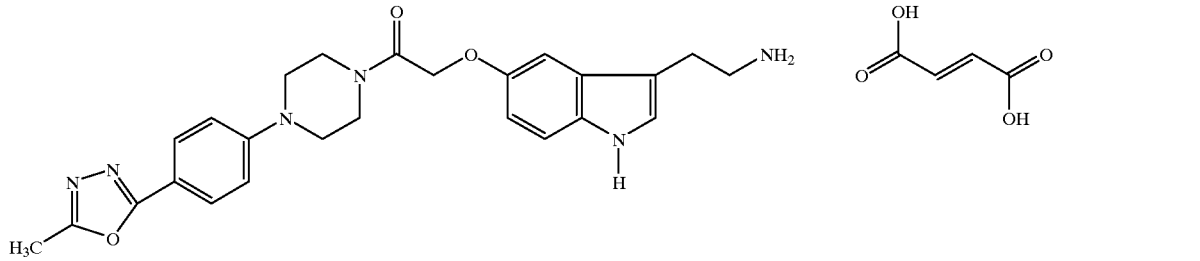

Compound 4 is prepared from intermediate 1B (205 mg; 0.62 mmol), acetyl chloride (0.16 ml; 2.23 mmol) and SerBOC acid (84 mg; 0.25 mmol) according to the procedure described for the preparation of Example 1.

$^1$H NMR DMSO-d6 (ppm): 2.55 s, 3H; 2.90–3.10 m, 4H; 3.30–3.40 m, 4H; 3.68 broad s, 4H; 4.83 s, 2H; 6.46 s, 2H; 6.80 d, 1H; 7.08–7.29 m, 5H; 10.86 s, 1H

| Elemental analysis $C_{29}H_{32}N_6O_7.1.6H_2O$ | | | |
|---|---|---|---|
| % calculated: | C 57.63 | H 5.87 | N 13.96 |
| % found: | C 58.02 | H 5.80 | N 13.56 |

Melting point: 145–150° C.

EXAMPLE 5

2-[3-(2-Aminoethyl)-1H-indol-5-yloxy]-1-{4-[4-(4,5-dihydrooxazol-2-yl)phenyl]piperazin-1-yl}ethanone Fumarate

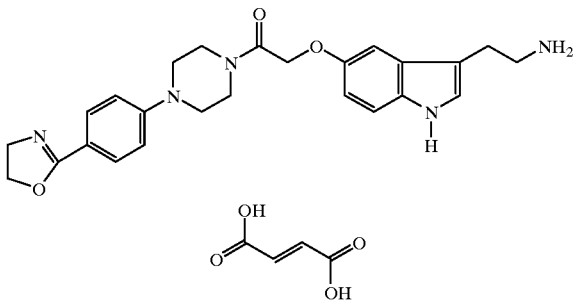

5A) N-tert-Butoxycarbonyl-4-[4-(4,5-dihydrooxazol-2-yl)phenyl]piperazine

A mixture of ethanolamine (0.91 ml; 15.0 mmol), glycerol (2.7 g), ethylene glycol (5.6 g) and potassium carbonate (2.1 g; 15.0 mmol) is heated at 105° C. for 30 min. The intermediate 1A (2.3 g; 8.04 mmol) is then added and the mixture is heated for 5 days at 105° C. The precipitate formed is filtered on sintered glass and washed with water and with petroleum ether to give compound 5A (988 mg; 37%) in the form of a beige solid.

5B) 4-[4-(4,5-Dihydrooxazol-2-yl)phenyl]piperazine

Compound 5A (826 mg; 2.49 mmol) in solution in toluene (20 ml) is treated, at room temperature, with trifluoroacetic acid (2.75 ml). After 1 h, the medium is evaporated to dryness and coevaporated 3 times with toluene. The product obtained is taken up in methanol (20 ml) and triethylamine (8 ml), stirred for 15 min at room temperature and finally evaporated to dryness. The solid obtained is purified by chromatography on a silica gel column eluted with a dichloromethane/methanol/ammonium hydroxide mixture in the proportions 90/9/1 to give the intermediate 5B.

5) 2-[3-(2-Aminoethyl)-1H-indol-5-yloxy]-1-{4-[4-(4,5-dihydrooxazol-2-yl)phenyl]piperazin-1-yl}ethanone Fumarate Compound 5 is prepared from intermediate 5B (576 mg; 2.48 mmol) and SerBOC acid (694 mg; 2.07 mmol) according to the procedure described for the preparation of Example 1 from 1C.

$^1$H NMR DMSO-d6 (ppm): 2.94 t, 2H; 3.05 t, 2H; 3.25–3.38 m, 4H; 3.55–3.72 m, 4H; 3.89 t, 2H; 4.33 t, 2H; 4.82 s, 2H; 6.45 s, 2H; 6.80 dd, 1H; 7.00 d, 2H; 7.14 d, 1H; 7.19 d, 1H; 7.26 d, 1H; 7.71 d, 2H; 10.84 s, 1H

| Elemental analysis $C_{29}H_{33}N_5O_7.2.9H_2O$ | | | |
|---|---|---|---|
| % calculated: | C 56.56 | H 6.35 | N 11.37 |
| % found: | C 56.84 | H 6.06 | N 11.35 |

Melting point: 170° C.

Mass spectrum: m/z 448 (MH$^+$)

6) 2-[3-(2-Aminoethyl)-1H-indol-5-yloxy]-1-[4-(4-oxazol-2-ylphenyl)piperazin-1-yl]ethanone Fumarate Compound 6 is prepared from intermediate 6A (54 mg; 0.16 mmol) and SerBOC acid (53 mg; 0.16 mmol) according to the procedure described for the preparation of Example 1 from 1C.

$^1$H NMR DMSO-d6 (ppm): 2.90–3.00 m, 2H; 3.00–3.10 m, 2H; 3.25–3.40 m, 4H; 3.59–3.74 m, 4H; 4.83 s, 2H; 6.81 dd, 1H; 7.08 d, 2H; 7.14 s, 1H; 7.21 s, 1H; 7.25–7.31 m, 2H; 7.83 d, 2H; 7.90 broad s, 3H; 8.11 s, 1H; 10.85 s, 1H

| Elemental analysis $C_{25}H_{27}N_5O_3.2.2HCl.3.5H_2O$ | | | |
|---|---|---|---|
| % calculated: | C 51.00 | H 6.20 | N 11.89 |
| % found: | C 51.21 | H 5.82 | N 11.70 |

Melting point: 64–66° C. (degradation)

Mass spectrum: m/z 446 (MH$^+$)

EXAMPLE 7

2-[3-(2-Aminoethyl)-1H-indol-5-yloxy]-1-[4-(4-benzothiazol-2-ylphenyl)piperazin-1-yl]ethanone Fumarate

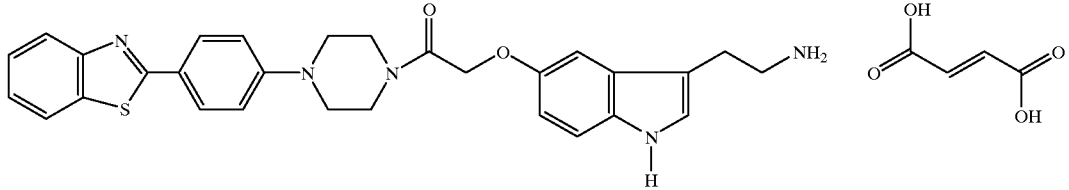

EXAMPLE 6

2-[3-(2-Aminoethyl)-1H-indol-5-yloxy]-1-[4-(4-oxazol-2-ylphenyl)piperazin-1-yl]ethanone Hydrochloride

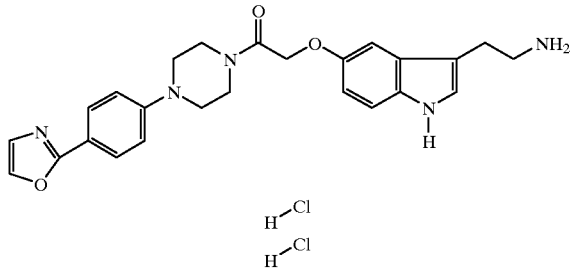

6A) 4-(4-Oxazol-2-ylphenyl)piperazine

Intermediate 5A (597 mg; 1.80 mmol) in solution in xylene (8 ml) is treated with 2,3-dichloro-5,6-dicyano-1,4-benzoquinone (450 mg; 1.98 mmol). The mixture is heated for 50 min under reflux and then evaporated to dryness.

The black solid obtained is purified by chromatography on a silica gel column eluted with a hexane/ethyl acetate mixture in the proportions 3/1 to give a yellow solid (59 mg; 10%). This compound is deprotected according to the procedure described for the preparation of compound 5B from compound 5A to give the trifluoroacetic acid salt of compound 6A in the form of a beige solid (54 mg; 100%).

2-Aminothiophenol (0.32 ml; 3.0 mmol) in solution in tetrahydrofuran (10 ml) is treated, under nitrogen and at room temperature, with sodium hydride (60% in oil) (480 mg; 12.0 mmol).

The medium is heated to 60° C. and then intermediate 1A (861 mg; 3.0 mmol) is added. The mixture is kept at 60° C. for 3 h 30 min and then cooled to 5° C. and neutralized by addition of ammonium chloride.

The mixture is extracted with ethyl acetate and then with dichloromethane. The organic phases are combined, dried over sodium sulfate and evaporated to dryness. The syrup obtained is purified by chromatography on a silica gel column eluted with a dichloromethane/ethyl acetate mixture in the proportions 20/1 to give the product of condensation (760 mg; 64%).

Compound 7 is prepared from the preceding intermediate which is deprotected and then condensed with SerBOC acid (170 mg; 0.51 mmol) according to the procedure described for the preparation of Example 1.

$^1$H NMR DMSO-d6 (ppm): 2.95–3.04 m, 4H; 3.30–3.45 m, 4H; 3.68 broad s, 4H; 4.84 s, 2H; 6.44 s, 2H; 6.80 dd, 1H; 7.08–7.29 m, 5H; 7.35–7.53 m, 2H; 7.92–7.98 m, 3H; 8.07 d, 1H; 10.85 s, 1H

| Elemental analysis $C_{29}H_{29}N_5O_2S.0.8C_4H_4O_4.1.3H_2O$ | | | |
|---|---|---|---|
| % calculated: | C 61.48 | H 5.57 | N 11.09 |
| % found: | C 61.02 | H 5.42 | N 10.73 |

Melting point: 156–160° C.

Mass spectrum: m/z 512 (MH$^+$)

EXAMPLE 8

2-[3-(2-Aminoethyl)-1H-indol-5-yloxy]-1-{4-[4-(2H-tetrazol-5-yl)phenyl]piperazin-1-yl}ethanone Hydrochloride

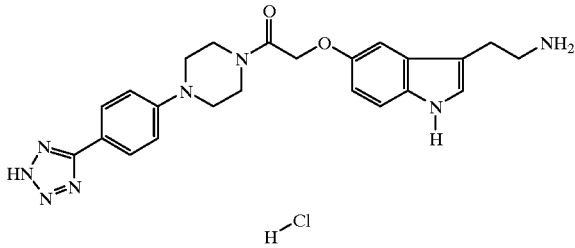

4-(4-{2-[3-(2-{N-tert-Butoxycarbonyl}amino-ethyl)-1H-indol-5-yloxy]acetyl}piperazin-1-yl)benzo-nitrile (J. Med. Chem., 1995, 38, 3602–3607) (400 mg; 0.79 mmol) in solution in xylene (5 ml) is treated, under nitrogen, with trimethyltin azide (310 mg; 1.50 mmol). The mixture is heated for 5 days at 110° C. and then the precipitate formed is filtered on sintered glass and washed with toluene to give a cream-colored solid.

This compound is purified by chromatography on a silica gel column eluted with a dichloromethane/methanol/ammonium hydroxide mixture in the proportions 85/14/1 to give a yellow powder (350 mg; 81%).

This intermediate is deprotected according to the conditions described for the preparation of compound 5B from compound 5A, to give compound 8 (209 mg; 73%) isolated in hydrochloride form.

$^1$H NMR DMSO-d6 (ppm): 2.95–3.05 m, 4H; 3.38 broad s, 4H; 3.67 broad s, 4H; 4.82 s, 2H; 6.80 dd, 1H; 7.11–7.28 m, 5H; 7.80–7.95 m, 5H; 10.84 s, 1H Melting point: 225–227° C.

Mass spectrum: 447 (MH$^+$)

EXAMPLE 9

2-[3-(2-Aminoethyl)-1H-indol-5-yloxy]-1-[4-(4-pyridin-4-ylphenyl)piperazin-1-yl]ethanone Fumarate

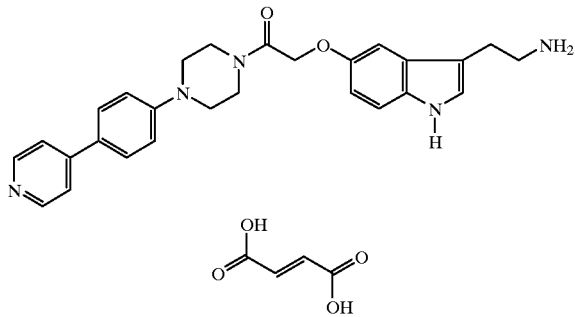

9A) 2-Chloro-1-[(4-hydroxyphenyl)piperazin-1-yl]ethanone

4-Hydroxyphenylpiperazine (8 g; 44.9 mmol) in solution in methyl ethyl ketone (43 ml), in the presence of potassium carbonate (15.5 g; 112 mmol) is treated, at 0° C. and dropwise with chloracetyl chloride (5.4 ml; 67.2 mmol).

After stirring for 1 h 30 min at 0° C., the medium is diluted in ethyl acetate, filtered on celite, washed with water and then with a sodium chloride solution. The organic phase is dried over sodium sulfate, filtered and evaporated.

The product obtained is purified by chromatography on a silica gel column eluted with a dichloromethane/methanol/ammonium hydroxide mixture in the proportions 95/4.5/0.5 to give compound 9A (8.2 g; 72%) in the form of a beige solid.

9B) 2-Chloro-1-[(4-trifluorosulfonate-phenyl)piperazin-1-yl]ethanone

Compound 9A (7.8 g; 30.6 mmol) in solution in dichloromethane (428 ml), in the presence of triethylamine (10.6 ml; 76.5 mmol) is treated, under nitrogen and at 0° C., with triflic anhydride (7.7 ml; 45.9 mmol).

After stirring for 1 h from 0° C. to room temperature, the medium is diluted with dichloromethane, washed with a sodium bicarbonate solution and then with a sodium chloride solution.

The organic phase is dried over sodium sulfate and then filtered and evaporated to dryness. The product obtained is purified by chromatography on a silica gel column eluted with a dichloromethane/acetone mixture in the proportions 100/1 to give product 9B (10.8 g; 91%).

9C) 2-[3-(2-{N-tert-Butoxycarbonylaminoethyl)-1H-indol-5-yloxy]-1-[4-(4-trifluorosulfonate-phenyl)piperazin-1-yl]ethanone 3-[2-(N-tert-Butoxycarbonyl)aminoethyl]-1H-indol-5-ol (J. Med. Chem., 1995, 38, 3602–3607) (3.5 g; 12.68 mmol) in solution in methyl ethyl ketone (140 ml), in the presence of potassium carbonate (4.37; 31.7 mmol) and potassium iodide (0.21 g; 1.26 mmol) is treated at room temperature with intermediate 9B (10.8 g; 27.9 mmol).

The mixture is heated under reflux for 8 h and then brought to room temperature and stirred overnight. The medium is diluted with ethyl acetate, washed with water and then with a sodium chloride solution. The organic phase is dried over sodium sulfate, filtered and evaporated to dryness.

The product obtained is purified by chromatography on a silica gel column eluted with a dichloromethane/ethyl acetate mixture in the proportions 9/1 for give product 9C (3.87 g; 49%).

9) 2-[3-(2-Aminoethyl)-1H-indol-5-yloxy]-1-[4-(4-pyridin-4-ylphenyl)piperazin-1-yl]ethanone A mixture of intermediate 9C (600 mg; 0.96 mmol), 4-pyridinylboronic acid (117 mg; 1.44 mmol), lithium chloride (121 mg; 2.88 mmol) and palladium tetrakis (155 mg; 0.134 mmol) in a mixture of dimethoxyethane (3.1 ml) and 2M sodium carbonate (1.3 ml) is heated at 105° C. and under nitrogen for 23 h. The medium is diluted with ethyl acetate, washed with sodium hydroxide (2N) and then with water and finally with a sodium chloride solution. The organic phase is dried over sodium sulfate, filtered and evaporated to dryness.

The product obtained is purified by chromatography on a silica gel column eluted with a dichloromethane/methanol/ammonium hydroxide mixture in the proportions 99/1/0.1 and then in the proportions 90/9/1 to give a syrup (259 mg; 49%).

This compound is deprotected under the conditions described for the preparation of compound 5B from compound 5A to give compound 9 (142 mg; 67%) isolated in fumarate form.

$^1$H NMR DMSO-d6 (ppm): 2.92 s, 2H; 3.03 s, 2H; 3.20–3.35 m, 4H; 3.66 d, 4H; 4.82 s, 2H; 6.41 s, 2H; 6.80 d, 1H; 7.08 d, 2H; 7.13 s, 1H; 7.18 s, 1H; 7.26 d, 1H; 7.50–7.65 m, 2H; 7.72 d, 2H; 8.54 s, 2H; 10.81 s, 1H

| Elemental analysis C₂₇H₂₉N₅O₂·1.1C₄H₄O₄·1.65H₂O | | | |
|---|---|---|---|
| % calculated: | C 61.53 | H 6.03 | N 11.43 |
| % found: | C 61.63 | H 5.85 | N 11.03 |

Melting point: 176° C.
Mass spectrum: m/z 456 (MH⁺)

EXAMPLE 10

2-[3-(2-Aminoethyl)-1H-indol-5-yloxy]-1-[4-(4-thiophen-2-ylphenyl)piperazin-1-yl]ethanone

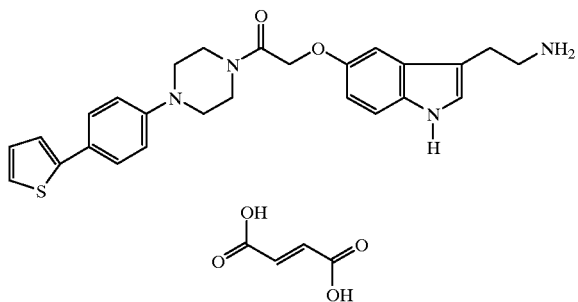

Compound 10 is prepared from intermediate 9C (600 mg; 0.96 mmol) and 2-thiopheneboronic acid (184 mg; 1.44 mmol) according to the procedure described for the preparation of Example 9.

¹H NMR DMSO-d6 (ppm): 2.86 t, 2H; 2.97 t, 2H; 3.18–3.26 m, 4H; 3.60–3.70 m, 4H; 4.81 s, 2H; 6.36 s, 1H; 6.80 dd, 1H; 7.00 d, 2H; 7.05–7.15 m, 2H; 7.16 d, 1H; 7.25 d, 1H; 7.33 d, 1H; 7.40 dd, 1H; 7.51 d, 2H; 10.78 s, 1H

| Elemental analysis C₂₆H₂₈N₄O₂S₁·0.5C₄H₄O₄·1H₂O | | | |
|---|---|---|---|
| % calculated: | C 62.27 | H 6.01 | N 10.44 |
| % found: | C 63.03 | H 5.85 | N 10.80 |

Melting point: 154–156° C.
Mass spectrum: m/z 461 (MH⁺)

EXAMPLE 11

2-[3-(2-Aminoethyl)-1H-indol-5-yloxy]-1-[4-(4-thiophen-3-ylphenyl)piperazin-1-yl]ethanone Fumarate

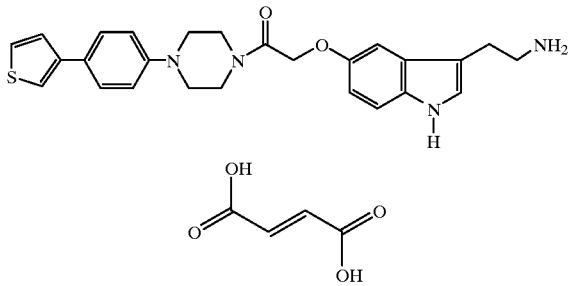

Compound 11 is prepared from intermediate 9C (600 mg; 0.96 mmol) and 3-thiopheneboronic acid (184 mg; 1.44 mmol) according to the procedure described for the preparation of Example 9.

¹H NMR DMSO-d6 (ppm): 2.90–3.05 m, 4H; 3.10–3.20 m, 4H; 3.65 broad s, 4H; 4.82 s, 2H; 6.41 s, 1H; 6.79 dd, 1H; 6.98 d, 2H; 7.15 dd, 2H; 7.25 d, 1H; 7.48 d, 1H; 7.56–7.60 m, 3H; 7.76 d, 1H; 10.82 s, 1H

| Elemental analysis C₂₆H₂₈N₄O₂S₁·0.6C₄H₄O₄·1.2H₂O | | | |
|---|---|---|---|
| % calculated: | C 62.22 | H 5.96 | N 10.22 |
| % found: | C 61.88 | H 5.78 | N 9.88 |

Melting point: 139–141° C.

The following examples illustrate compositions according to the invention. In these examples, the term "active component" designates one or more (generally one) of the compounds of formula (I) according to the present invention.

Tablets

They can be prepared by direct compression or via wet granulation. The direct compression procedure is preferred but it may not be suitable in all cases depending on the doses and the physical properties of the active component.

| A - By direct compression | |
|---|---|
| | mg for 1 tablet |
| active component | 10.0 |
| microcrystalline cellulose B.P.C. | 89.5 |
| magnesium stearate | 0.5 |
| | 100.0 |

The active component is passed through a sieve with a mesh opening of side 250 μm, it is mixed with the excipients and the mixture is compressed with the aid of 6.0 mm dies. It is possible to prepare tablets having other mechanical strengths by modifying the compression weight with the use of appropriate dies.

| B-wet granulation | |
|---|---|
| | mg for one tablet |
| active component | 10.0 |
| lactose Codex | 74.5 |
| starch Codex | 10.0 |
| pregelatinized corn starch Codex | 5.0 |
| magnesium stearate | 0.5 |
| weight at compression | 100.0 |

The active component is passed through a sieve with a mesh opening of 250 μm and mixed with the lactose, starch and pregelatinized starch. The mixed powders are moistened with purified water, converted to granules, dried, sieved and mixed with magnesium stearate. The lubricated granules are made into tablets as for the direct compression formulas. It is possible to apply on the tablets a coating film by means of appropriate film-forming materials, for example methyl cellulose or hydroxypropylmethylcellulose, according to conventional techniques. It is also possible to coat the tablets with sugar.

Capsules

| | mg for one capsule |
|---|---|
| active component | 10.0 |
| * starch 1500 | 89.5 |
| magnesium stearate Codex | 0.5 |
| filling-up weight | 100.0 |

* a directly compressible form of starch which is obtained from the company Colorcon Ltd, Orpington, Kent, United Kingdom.

The active component is passed through a sieve with a mesh opening of 250 μm and mixed with the other substances. The mixture is introduced into hard gelatin capsules No. 2 on an appropriate filling machine. It is possible to prepare other dosage units by modifying the filling-up weight and, when necessary, by changing the size of the capsule.

Syrup

| | mg per 5 ml dose |
|---|---|
| active component | 10.0 |
| sucrose Codex | 2750.0 |
| glycerin Codex | 500.0 |
| buffer | |
| flavoring | |
| coloring | q.s. |
| preservative | |
| distilled water | 5.0 |

The active component, buffer, flavoring, coloring and preservative are dissolved in a portion of the water and glycerin is added. The remainder of the water is heated to 80° C. and the sucrose is dissolved therein and the mixture is then cooled. The two solutions are combined, the volume is adjusted and the solution is mixed. The syrup obtained is clarified by filtration.

Suppositories

| | |
|---|---|
| active component | 10.0 mg |
| * Witepsol H15 balance for | 1.0 g |

* brand marketed for Adeps Solidus of the European Pharmacopeia.

A suspension of the active component is prepared in Witepsol H15 and it is introduced into an appropriate machine with 1 g suppository molds.

Liquid for administration by intravenous injection

| | g/l |
|---|---|
| active component | 2.0 |
| water for injection Codex balance for | 1000.0 |

It is possible to add sodium chloride in order to adjust the tonicity of the solution and to adjust the pH to the maximum stability and/or in order to facilitate the dissolution of the active component by means of a dilute alkali or acid or by adding appropriate buffer salts. The solution is prepared, it is clarified and it is introduced into ampoules of appropriate size which are sealed by melting the glass. It is also possible to sterilize the liquid for injection by heating in an autoclave according to one of the acceptable cycles. It is also possible to sterilize the solution by filtration and to introduce into a sterile ampoule under aseptic conditions. The solution may be introduced into the ampoules in a gaseous atmosphere.

Cartridges for inhalation

| | g/cartidge |
|---|---|
| micronized active component | 1.0 |
| lactose Codex | 39.0 |

The active component is micronized in a grinder using fluid energy and converted to fine particles before mixing with lactose for tablets in a high-energy mixer. The pulverulent mixture is introduced into hard gelatin capsules No. 3 in an appropriate encapsulating machine. The content of the cartridges is administered with the aid of a powder inhaler.

Pressurized aerosol with metering valve

| | mg/dose | for 1 packet |
|---|---|---|
| micronized active component | 0.500 | 120 mg |
| oleic acid Codex | 0.050 | 12 mg |
| trichlorofluoromethane for pharmaceutical use | 22.25 | 5.34 g |
| dichlorodifluoromethane for pharmaceutical use | 60.90 | 14.62 g |

The active component is micronized in a grinder using fluid energy and converted to fine particles. The oleic acid is mixed with the trichlorofluoromethane at a temperature of 10–15° C. and the micronized medicament is introduced into the solution with the aid of a mixer with a high shearing effect. The suspension is introduced in a measured quantity into aluminum aerosol cans to which appropriate metering valves delivering a dose of 85 mg of suspension are attached; the dichlorodifluoromethane is introduced into the cans by injection through valves.

Pharmacological Properties

The derivatives of the present invention are very selective agonists for the $5\text{-HT}_{1B/1D}$ receptors and in particular for the human $5\text{-HT}_{1D}$ and $5\text{-HT}_{1B}$ receptors. The study of the binding of a few examples of compounds of the present invention with these receptors was carried out according to the method described by P. PAUWELS and C. PALMIER (Neuropharmacology, 33, 67, 1994). This method shows that these compounds have an affinity of less than 100 nM for the human $5HT_{1D}$ and $5HT_{1B}$ receptors. The derivatives of the present invention are in addition capable, like serotonin, of inducing the constriction of the rings of rabbit saphenous vein which is mediated by the $5HT_{1B}$ receptors. The technique used was adapted from Van Heuven-Nolsen D. et al. (Eur. J. Pharmacol., 191, 375, 1990) and from Martin G. R. and McLennan (Naunyn-Schmideberg's Arch. Pharmacol., 342, 111, 1990).

These pharmacological results illustrate the advantage of the compounds of the present invention which are novel and potent $5\text{-HT}_{1B}$ and $5\text{-HT}_{1D}$ receptor agonists.

In human therapy, the compounds of general formula (I) according to the invention are particularly useful for the treatment and prevention of serotonin-related disorders at the level of the central nervous system and of the vascular system. These compounds can therefore be used in the treatment and prevention of depression, obsessive-compulsive disorders, bulimia, aggressiveness, alcoholism, nicotine addiction, hypertension, nausea, sexual dysfunction, antisocial behavior, anxiety, migraine, spasticity, Alzheimer's disease and memory disorders.

What is claimed is:

1. A compound selected from those corresponding to formula (I)

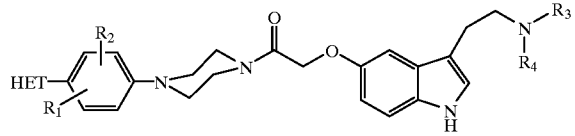

(I)

in which,

HET represents a heterocycle chosen from the group consisting of

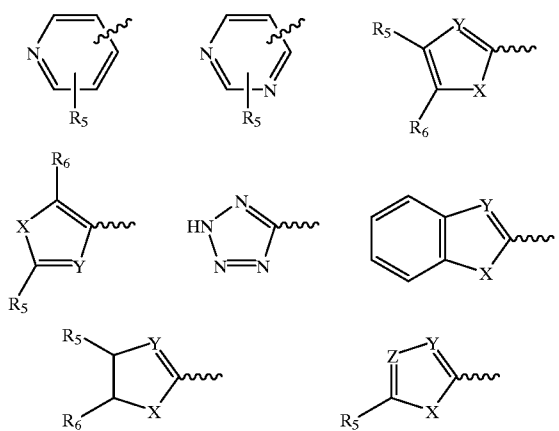

$R_1$ and $R_2$ which are identical or different, represent a hydrogen atom, or a substituent $R'_1$, $CF_3$, $CH_2CF_3$, $C_6H_5$, $CH_2C_6H_5$, OH, $OR'_1$, SH, $SR'_1$, Cl, F, Br, I, CN, $NH_2$, $NHR'_1$, $NR'_1R'_2$, $NO_2$, NH—$NH_2$, NH—$NHR'_1$, NHOH, $NHCO_2R'_1$, $NHCONH_2$, $NHCONR'_1R'_2$, $NHSO_2R'_1$, $SO_2R'_1$, $SO_2NH_2$, $SO_2NHR'_1$, $COR'_1$, $CO_2R'_1$, $CONH_2$, $CONHR'_1$, or $CONR'_1R'_2$ which may be at the ortho or meta position on the aromatic ring, $R_3$ and $R_4$, which are identical or different, represent a hydrogen atom, a linear or branched carbon-containing radical having 1 to 6 carbon atoms, benzyl, or phenethyl, Y and Z, which are identical or different, represent CH or N, X represents O, S, or $NR_7$, $R_5$, $R_6$, $R_7$, which are identical or different, represent a hydrogen atom, linear or branched alkyl having 1 to 6 carbon atoms, or phenyl which is optionally substituted with linear or branched alkyl having 1 to 6 carbon atoms, a halogen atom, $CF_3$, $OCH_3$, CN, or $NO_2$, $R'_1$ and $R'_2$, which are identical or different, represent linear or branched alkyl having 1 to 6 carbon atoms, or phenyl which is optionally substituted with linear or branched alkyl of 1 to 6 carbon atoms, Cl, Br, F, I, $OCH_3$, OH, $NO_2$, or $SCH3$, or its pharmaceutically-acceptable salts, and hydrates.

2. A compound according to claim 1, wherein $R_1$, $R_2$, $R_3$, and $R_4$ each represent a hydrogen atom.

3. A compound according to claim 1, wherein HET represents a pyridyl or pyrimidyl residue.

4. A compound according to claim 1, wherein HET represents a 5-membered heterocycle containing 1 to 3 heteroatoms chosen from O, S, and N.

5. A compound according to claim 1, in the form of a salt chosen from the group consisting of hydrochlorides, hydrobromides, sulfates, fumarates, maleates, methanesulfonates, and succinates.

6. A pharmaceutical composition containing, as active ingredient, at least one compound according to claim 1 and a pharmaceutically-acceptable excipient.

7. A compound according to claim 2, wherein HET represents a pyridyl or pyrimidyl residue.

8. A compound according to claim 2, wherein HET represents a 5-membered heterocycle containing 1 to 3 heteroatoms chosen from O, S, and N.

9. A compound according to claim 3, in the form of a salt chosen from the group consisting of hydrochlorides, hydrobromides, sulfates, fumarates, maleates, methanesulfonates, and succinates.

10. A pharmaceutical composition containing, as active ingredient, at least one compound according to claim 7 and a pharmaceutically-acceptable excipient.

11. Method of preparing a compound of claim 1, wherein an intermediate of formula (II)

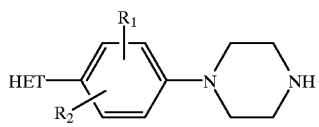

(II)

is reacted with a carboxylic acid or a carboxylic acid derivative of formula (III)

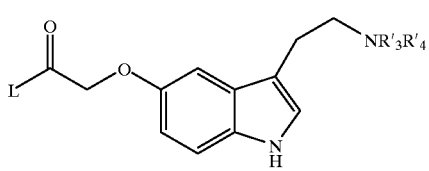

(III)

in which $R'_3$ and $R'_4$ are identical to $R_3$ and $R_4$ as defined in formula (I), or $R'_3$ and $R'_4$ are precursors of or protecting groups for $R_3$ and $R_4$ which will be converted to $R_3$ and $R_4$ following the condensation of (II) with (III), and L represents OH, Cl, O-alkyl, where the group —C(=O)L represents the activated form of a carboxylic acid.

12. A method of treating a living body in need thereof for the treatment 5-$HT_{1B/1D}$ receptor associated diseases or for the treatment of migraine, vascular facial pain or chronic vascular cephalalgia, or for the treatment of depression, aggressiveness, alcoholism, nausea, sexual dysfunction, anxiety, comprising the step of administering to the living body an effective amount of a compound of claim 1.

13. A method of treating a living body in need thereof for the treatment 5-$HT_{1B/1D}$ receptor associated diseases or for the treatment of migraine, vascular facial pain or chronic vascular cephalalgia, or for the treatment of depression, aggressiveness, alcoholism, nausea, sexual dysfunction, anxiety, comprising the step of administering to the living body an effective amount of a compound of claim 7.

* * * * *